(12) United States Patent
Burns et al.

(10) Patent No.: US 7,276,254 B2
(45) Date of Patent: Oct. 2, 2007

(54) EMULSION/AGGREGATION POLYMERIC MICROSPHERES FOR BIOMEDICAL APPLICATIONS AND METHODS OF MAKING SAME

(75) Inventors: Patricia Ann Burns, Milton (CA); Raj D. Patel, Oakville (CA); Hadi Khan Mahabadi, Toronto (CA); Ronald F. Ziolo, Webster, NY (US)

(73) Assignee: Xerox Corporation, Stamford, CT (US)

(*) Notice: Subject to any disclaimer, the term of this patent is extended or adjusted under 35 U.S.C. 154(b) by 878 days.

(21) Appl. No.: 10/063,656

(22) Filed: May 7, 2002

(65) Prior Publication Data

US 2003/0211035 A1 Nov. 13, 2003

(51) Int. Cl.
- A61K 9/14 (2006.01)
- A61K 51/00 (2006.01)
- A61K 9/16 (2006.01)
- A61M 36/14 (2006.01)
- A61B 5/055 (2006.01)

(52) U.S. Cl. ............ 424/489; 424/1.29; 424/9.32; 424/497

(58) Field of Classification Search ........ 424/501, 424/1.25, 1.33, 1.29, 489, 9.32; 428/401; 264/41; 516/11, 16
See application file for complete search history.

(56) References Cited

U.S. PATENT DOCUMENTS

| | | |
|---|---|---|
| 3,590,000 A | 6/1971 | Palermiti et al. |
| 3,655,374 A | 4/1972 | Palermiti et al. |
| 3,720,617 A | 3/1973 | Chatterji et al. |
| 3,944,493 A | 3/1976 | Jadwin et al. |
| 3,983,045 A | 9/1976 | Jugle et al. |
| 4,007,293 A | 2/1977 | Mincer et al. |
| 4,079,014 A | 3/1978 | Burness et al. |
| 4,138,383 A * | 2/1979 | Rembaum et al. .......... 524/809 |
| 4,243,694 A | 1/1981 | Mansukhani |
| 4,394,430 A | 7/1983 | Jadwin et al. |
| 4,444,961 A | 4/1984 | Timm |
| 4,560,635 A | 12/1985 | Hoffend et al. |
| 4,609,689 A | 9/1986 | Schwartz et al. |
| 4,911,830 A | 3/1990 | Bromley et al. |
| 4,956,128 A | 9/1990 | Hommel et al. |
| 4,981,625 A | 1/1991 | Rhim et al. |
| 5,078,994 A * | 1/1992 | Nair et al. ............... 424/501 |
| 5,160,745 A | 11/1992 | DeLuca et al. |
| 5,260,002 A | 11/1993 | Wang |
| 5,278,020 A | 1/1994 | Grushkin et al. |
| 5,290,654 A | 3/1994 | Sacripante et al. |
| 5,308,734 A | 5/1994 | Sacripante et al. |
| 5,344,738 A * | 9/1994 | Kmiecik-Lawrynowicz et al. |
| 5,346,797 A | 9/1994 | Kmiecik-Lawrynowicz et al. |
| 5,348,832 A | 9/1994 | Sacripante et al. |
| 5,364,729 A | 11/1994 | Kmiecik-Lawrynowicz et al. |
| 5,366,841 A | 11/1994 | Patel et al. |
| 5,370,963 A | 12/1994 | Patel et al. |
| 5,370,964 A | 12/1994 | Patel et al. |
| 5,376,347 A | 12/1994 | Ipponmatsu et al. |
| 5,403,693 A | 4/1995 | Patel et al. |
| 5,405,728 A | 4/1995 | Hopper et al. |
| 5,418,108 A | 5/1995 | Kmiecik-Lawrynowicz et al. |
| 5,496,676 A | 3/1996 | Croucher et al. |
| 5,501,935 A | 3/1996 | Patel et al. |
| 5,527,658 A | 6/1996 | Hopper et al. |
| 5,554,480 A | 9/1996 | Patel et al. |
| 5,585,215 A | 12/1996 | Ong et al. |
| 5,593,807 A | 1/1997 | Sacripante et al. |
| 5,604,706 A | 2/1997 | Hurt et al. |
| 5,643,506 A | 7/1997 | Rourke |
| 5,648,100 A | 7/1997 | Boschetti et al. |
| 5,650,255 A | 7/1997 | Ng et al. |
| 5,650,256 A | 7/1997 | Veregin et al. |
| 5,665,382 A * | 9/1997 | Grinstaff et al. ............ 424/450 |
| 5,723,269 A | 3/1998 | Akagi et al. |
| 5,853,944 A | 12/1998 | Foucher et al. |
| 5,869,216 A | 2/1999 | Ong et al. |
| 5,902,710 A | 5/1999 | Ong et al. |
| 5,919,595 A | 7/1999 | Mychajlowskij et al. |
| 5,942,209 A * | 8/1999 | Leavitt et al. ............ 424/1.25 |
| 5,945,245 A | 8/1999 | Mychajlowskij et al. |
| 6,039,970 A * | 3/2000 | Callegaro et al. .......... 424/434 |

(Continued)

FOREIGN PATENT DOCUMENTS

WO WO 01/70132 A2 9/2001

OTHER PUBLICATIONS

Burns et al., "Emulsion/Aggregation Technology: A Process for Preparing Microspheres of Narrow Polydispersity", The Xerox Research Centre of Canada, Mississauga, Canada.

(Continued)

*Primary Examiner*—Michael G. Hartley
*Assistant Examiner*—Blessing Fubara
(74) *Attorney, Agent, or Firm*—Oliff & Berridge, PLC

(57) ABSTRACT

A method of forming polymeric microspheres for biomedical applications includes forming polymeric microspheres by an emulsion/aggregation process from a precursor monomer species, and treating the polymeric microspheres to attach a biomedical functional material to the polymeric microspheres, where the polymeric microspheres have an average particle diameter of from about 1 to about 15 microns with a narrow particle geometric size distribution. The biomedical functional material may be, for example, a radioactive material, a radioactive precursor material, a bioactive agent, or a ligand.

28 Claims, No Drawings

U.S. PATENT DOCUMENTS

| | | | |
|---|---|---|---|
| 6,143,457 | A | 11/2000 | Carlini et al. |
| 6,207,171 | B1 | 3/2001 | Payne et al. |
| 6,238,702 | B1 | 5/2001 | Berde et al. |
| 6,294,606 | B1 | 9/2001 | Chen et al. |
| 6,348,561 | B1 | 2/2002 | Mychajlowskij et al. |
| 6,579,588 | B2 * | 6/2003 | Waid .......................... 428/41.8 |
| 2002/0010127 | A1 | 1/2002 | Oshlack et al. |

OTHER PUBLICATIONS

Conti et al., "Use of Polylactic Acid for the Preparation of Microparticulate Drug Delivery Systems", J. Microencapsulation, vol. 9, No. 2, pp. 153-166, 1992.

Cohen et al., "Microparticulate Systems for the Delivery of Proteins and Vaccines" Marcel Dekker Inc. 1996.

Amsden et al., "An Examination of Factors Affecting the Size, Distribution and Release Characteristics of Polymer Microbeads Made Using Electrostatics", Journal of Controlled Release, vol. 43, pp. 183-196, 1997.

Baker, "Controlled Release of Biologically Active Agents" John Wiley & Sons, 1987.

Ishikawa, et al., "Effect of Particle Size on Phagocytosis of Latex Particles by Guinea-Pig Polymorphonuclear Leucocytes" J. Biomater. Sci., Polymer Ed., vol. 2, No. 1, pp. 53-60, 1991.

Kamiyama et al., "Micron-Sized Polymeric Microsphere by Suspension Polymerization", Journal of Applied Polymer Science, vol. 50, pp. 107-113, 1993.

O'Donnell et al., "Properties of Multiphase Microspheres of Poly(D,L-lactic-co-glycolic acid) Prepared by a Potentiometric Dispersion Technique" J. Microencapsulation, 1995, vol. 12, No. 2, pp. 155-163, 1995.

Reyderman et al., "Novel Methods of Microparticulate Production: Application to Drug Delivery", Pharmaceutical Development and Technology, vol. 1(3), pp. 223-229, 1996.

Shiga et al., "Preparation of Poly(D,L,-lactide) and Copoly(lactide-glycolide) Microspheres of Uniform Size", J. Pharm. Pharmacol. vol. 48, pp. 891-895, 1996.

Sansdrap et al., "Influence of Manufacturing Parameters on the Size Characteristics and the Release Profiles of Nifedipine from Poly(DL-lactide-co-glycolide) Microspheres", International Journal of Pharmaceutics, vol. 98, pp. 157-164, 1993.

Sosnowski et al., "Synthesis of Bioerodible Poly(e-caprolactone) Latexes and Poly(D,L-lactide) Microspheres by Ring-Opening Polymerization", Journal of Bioactive and Compatible Polymers, vol. 9, pp. 345-366, 1994.

Leelarasamee et al., "A Method for the Preparation of Polytactic Acid Microcapsules of Controlled Particle Size and Drug Loading", J. Microencapsulation, vol. 5, No. 2, pp. 147-157, 1988.

House, "Modern Synthetic Reactions", W. A. Benjamin, Inc., 2$^{nd}$ Ed., Chapter 8, p. 422-491, 1972.

Beaujeux et al., "Trisacryl Gelatin Microspheres for Therapeutic Embolization, II: Preliminary Clinical Evaluation in Tumors and Arteriovenous Malformations", American Journal of Neuroradiology, vol. 17, pp. 541-548, 1996.

Eskridge et al., "Preoperative Endovascular Embolization of Craniospinal Hemangioblastomas", American Journal of Neuroradiology, vol. 17, pp. 525-531, 1996.

Young et al., "Methods of Renal Blood Flow Measurement", Urological Research, vol. 24, No. 3, pp. 149-160, 1996.

Leung et al., "Radiation Pneumonitis After Selective Internal Radiation Treatment with Intraarterial ) $^{90}$Yttrium-Microspheres for Inoperable Hepatic Tumors", Int. J. Radiation Oncology Biol. Phys., vol. 33, No. 4, pp. 919-924, 1995.

Ho et al., "Clinical Evaluation of the Partition Model for Estimating Radiation Doses From Yttrium-90 Microspheres in the Treatment of Hepatic Cancer", European Journal of Nuclear Medicine, vol. 24, No. 3, pp. 293-298, 1997.

* cited by examiner

EMULSION/AGGREGATION POLYMERIC MICROSPHERES FOR BIOMEDICAL APPLICATIONS AND METHODS OF MAKING SAME

BACKGROUND OF THE INVENTION

1. Field of Invention

The invention relates to polymeric microspheres, including magnetic and/or superparamagnetic polymeric microspheres, useful for biomedical applications. The polymeric microspheres of the present invention are generally of small size, about 1-15 microns, and are generally of a narrow particle or geometric size distribution. The present invention also relates to processes, particularly emulsion/aggregation polymerization processes, useful for making such polymeric microspheres.

2. Description of Related Art

Polymeric microspheres, i.e., microspheres formed (at least in part) from polymer, have found a variety of uses in the medical and industrial areas. Furthermore, biodegradable polymers have been the subject of numerous studies in controlled drug delivery (Conti et al., J. Microencapsulation 9:153 (1992); Cohen and Bernstein, Microparticulate Systems for the Delivery of Proteins and Vaccines (Marcel Dekker Inc. 1996)). As drug carriers, microspheres formed from biodegradable polymer(s) have the advantages of providing a large surface area, being easily injected, and not requiring removal after completion of drug release. When used as an injectable drug delivery device, it has been found that drug release rate and microsphere interaction with cells is strongly dependent on the size distribution of the microspheres (Amsden and Goosen, J. Contr. Rel. 43:183 (1997); Baker, Controlled Release of Biologically Active Agents (John Wiley 1987); Ishikawa. et al., J. Biomater. Sci., Polymer Ed. 2:53 (1991)).

Microspheres, particularly polymeric microspheres, also have found use in a wide range of other biological, medical and industrial uses. For example, microspheres having a narrow size distribution have found uses in such areas as immunoassays, cell separation processes, cancer therapy, diagnostic testing, and the like. In the biological and medical contexts, such polymeric microspheres are finding increasing uses in both in vivo and in vitro applications. Likewise, polymeric microspheres are finding increasing uses in laboratory testing, analysis and screening procedures.

Accordingly, there are numerous publications disclosing studies directed towards developing methods to prepare polymeric microspheres under conditions that allow for controlling the average particle size, and particle size distribution, of the microspheres. These methods include dispersion polymerization of the monomer, potentiometric dispersion of dissolved polymer within an emulsifying solution followed by solvent evaporation, electrostatically controlled extrusion, injection of dissolved polymer into an emulsifying solution through a porous membrane followed by solvent evaporation (see, e.g., Kuriyama et al., J. Appl. Poly. Sci. 50:107 (1993); Rembaum et al., U.S. Pat. No. 4,138,383; O'Donnell et al., J. Microencaps. 12:155 (1995); Hommel et al., U.S. Pat. No. 4,956,128; Amsden and Goosen, J. Contr. Rel. 43:183 (1997); Reyderman and Stavchansky, Pharm. Dev. Technol. 1:223 (1996); Ipponmatsu et al., U.S. Pat. No. 5,376,347; Shiga et al., J. Pharm. Pharmacol. 48:891 (1996).

Additional methods include vibratory excitation of a laminar jet of monomeric material flowing in a continuous liquid medium containing a suitable suspending agent, irradiation of slowly thawing frozen monomer drops, emulsification and evaporation, emulsification and evaporation using a high shear apparatus and a high hydrophobic phase to hydrophilic phase ratio, controlled polymerization in a solvent, non-solvent mixture, extrusion into a high shear air flow, and continuous injection of dissolved polymer into a flowing non-solvent through a needle oriented in parallel to the direction of flow of the non-solvent (see also, e.g., Timm and Coleman, U.S. Pat. No. 4,444,961; Rhim et al. U.S. Pat. No. 4,981,625; Sansdrap and Moes, Int. J. Pharm. 98:157 (1993); Rourke, U.S. Pat. No. 5,643,506; Sosnowski et al., J. Bioact. Compat. Polym. 9:345 (1994); Wang, U.S. Pat. No. 5,260,002; Leelarasamee et al., J. Microencaps. 5:147 (1988)).

As set forth below, each of these published methods has shortcomings that curtails the utility of the formed-microspheres in various applications, and particularly when the methods are applied to the continuous production of uniformly sized microspheres, including biocompatible, biodegradable, drug-loaded microspheres.

Conventional monomer polymerization processes do not allow the easy inclusion of a bioactive agent or functional material within the formed polymeric microsphere (Kuriyama et al., J. Appl. Poly. Sci. 50:107 (1993); Rembaum et al., U.S. Pat. No. 4,138,383; Timm and Coleman, U.S. Pat. No. 4,444,961; Rhim et al. U.S. Pat. No. 4,981,625; Sosnowski et al., J. Bioact. Compat. Polym. 9:345 (1994)). For example, where the conventional methods are used to incorporate a functional compound such as a drug or other material in or on the microsphere, the polymerization conditions may result in the deactivation of the functional compound, or the functional compound may become included in the polymer backbone.

The electrostatic extrusion process does not produce uniformly sized microspheres of a comparatively small diameter (Hommel et al., U.S. Pat. No. 4,956,128; Amsden and Goosen, J. Contr. Rel. 43:183 (1997); Reyderman and Stavchansky, Pharm. Dev. Technol. 1:223 (1996)).

The emulsification process of Sansdrap and Moes, Int. J. Pharm. 98:157 (1993), produces relatively narrow size distributions but is performed in batch mode and in a very small scale (500 milliliters).

Injecting a polymer dissolved in a volatile solvent through a porous membrane produced microspheres of a narrow size distribution but the size of the microspheres is controlled virtually completely by the size of the pores in the glass membrane used, and only low viscosity polymer solutions were possible (Ipponmatsu et al., U.S. Pat. No. 5,376,347; Shiga et al., J. Pharm. Pharmacol. 48:891 (1996)).

The high shear emulsification process of Rourke, U.S. Pat. No. 5,643,506, cannot produce a wide range of microsphere average sizes having a narrow size distribution.

Finally, the injection method of Leelarasamee et al., J. Microencaps. 5:147 (1988), involves the use of a non-solvent, which requires additional, and difficult, removal steps that would decrease the incorporation efficiency of a lipophilic agent, and could not produce narrow microsphere size distributions. Furthermore, Leelarasamee et al. does not demonstrate the ability to control the microsphere average diameter through manipulation of the process parameters.

Thus, a need exists for a simple and reliable method for producing uniformly-sized microspheres. Furthermore, it is desirable to be able to produce uniformly sized microspheres in a continuous fashion in such a manner that the size of the microspheres is easily controllable, that the process is scaleable to large production, and that allows the use of volatile solvents.

The present invention provides methods suitable for preparing microspheres. These methods address the problems associated with the existing procedures, offer significant advantages when compared to existing procedures, and in addition, provide other, related advantages.

SUMMARY OF THE INVENTION

These and other objects are achieved by the present invention, which provides an emulsion/aggregation process for producing polymeric microspheres. The polymeric microspheres exhibit a very narrow particle or geometric size distribution, and have particle sizes making them particularly useful for biomedical applications. Depending on the desired use, the polymeric microspheres can be subjected to a suitable treatment, which enables their use in the desired biomedical application.

The methods of the present invention form polymeric microspheres, which are suitable for use in a wide range of medical, biological, laboratory, and industrial applications. For example, the microspheres are useful in the delivery of bioactive agents for animal, aquarian and human use, as a means of radio-imaging tissue, for the controlled release of agro-chemicals, in immunoassays, in cell separation processes, in cancer therapy, in diagnostic testing, and the like.

In particular, the present invention provides a method of forming polymeric microspheres for biomedical applications, comprising:

forming polymeric microspheres by an emulsion/aggregation process from a precursor monomer species; and treating said polymeric microspheres to attach a biomedical functional material to said polymeric microspheres, wherein said polymeric microspheres have an average particle diameter of from about 1 to about 15 microns with a narrow particle geometric size distribution.

In one embodiment, the emulsion/aggregation process comprises: forming a polymeric resin from said precursor monomer species; aggregating said polymeric resin into polymeric particles; coalescing said polymeric particles into polymeric microspheres; and optionally isolating said polymeric microspheres.

In another embodiment, the emulsion/aggregation process comprises: forming a polymeric resin from said precursor monomer species; forming an emulsion comprising said polymeric resin; coalescing said polymeric resin into polymeric microspheres; and optionally isolating said polymeric microspheres.

In a still further embodiment, the emulsion/aggregation process comprises: providing a polyester resin formed from said monomeric species; dispersing said polyester resin an aqueous media by heating in water, to provide a suspension of suspended particles of said polyester resin; homogenizing said suspension; aggregating said homogenized suspension by adding a cationic metal salt and optional additives to form aggregated and coalesced particles by heating the aggregates near, and preferably below, the glass transition temperature of the polyester resin, to form polymeric microspheres; and optionally isolating said polymeric microspheres.

In a still further embodiment, the emulsion/aggregation process comprises: providing a polyester resin formed from said monomeric species; dispersing said polyester resin an aqueous media comprising an anionic surfactant, to provide a suspension of suspended particles of said polyester resin; homogenizing said suspension; aggregating said homogenized suspension by adding a cationic surfactant and optional additives to form aggregates; coalescing said aggregates by heating the aggregates above a glass transition temperature of the polyester resin, to form polymeric microspheres; and optionally isolating said polymeric microspheres.

If desired, a magnetic and/or superparamagnetic material may be incorporated into the polymeric microspheres to give the polymeric microspheres magnetic and/or superparamagnetic properties.

Further, if desired, a suitable colorant (which may be fluorescent or not), or other suitable visible or non-visible label, taggant, identifier, or the like may be incorporated into the polymeric microspheres for their known purposes.

DETAILED DESCRIPTION OF PREFERRED EMBODIMENTS

The present invention provides a process for forming microspheres. The process includes forming suitable particles (polymeric microspheres) in an emulsion/aggregation process, and then subjecting the formed particles (polymeric microspheres) to at least one suitable treatment, which enables use of the microspheres in the desired biomedical or other application.

In a first preferred embodiment, the particles are comprised of emulsion/aggregation (E/A) particles, i.e., particles prepared by the known emulsion/aggregation technique. Major advantages in the use of E/A particles as the polymeric microspheres are that E/A particles have a very narrow particle size distribution, which provide more uniform movement and properties of the particles, less likelihood of agglomeration problems during use, and minimum particle size classification subsequent to formation. The E/A processes are particularly suited for making such microspheres, as the processes are efficient in forming microspheres of the desired size range, with narrow particle size distribution. Another advantage of E/A particles, and the polymerization processes to make such particles, is the ability to more easily incorporate additives, such as colorants (either conventional, fluorescent, or the like), magnetic and/or superparamagnetic materials, etc., into the microspheres. The EA process also provide a greater degree of flexibility in forming desired microspheres, as the E/A processes broaden the range of types of resins that can be used, and provide the ability to begin with resins that have functional groups in them or can easily be formed by reactions of the surface of the microsphere once formed.

Emulsion/aggregation processes for making particles, for example colored particles for use in electrophotographic and other imaging processes, in which the particles are achieved via aggregation as opposed to particle size reduction, are well know. Such E/A processes generally include the steps of, e.g., emulsion, aggregation, coalescence, washing and drying. For example, emulsion/aggregation processes for the preparation of toner particles are illustrated in a number of Xerox patents, the disclosures of which are totally incorporated herein by reference, such as U.S. Pat. Nos. 5,290,654, 5,278,020, 5,308,734, 5,370,963, 5,370,964, 5,344,738, 5,403,693, 5,418,108, 5,364,729, and 5,346,797. Also of interest may be U.S. Pat. Nos. 5,348,832, 5,405,728, 5,366,841, 5,496,676, 5,527,658, 5,585,215, 5,650,255, 5,650,256, 5,501,935, 6,294,606, 5,593,807, 5,604,706, 5,853,944, 5,919,595, 6,348,561, and 5,945,245, the entire disclosures of which are also incorporated herein by reference. The E/A process is not limited in the use of certain polymers for toner particles, although polyesters and acrylic based polymers (e.g., styrene acrylate) are convenient for use in the process, the use of polyesters having the further advantage of not requiring the use of any surfactants in making the particles.

Fluoropolymers may also be used, these polymers showing excellent charge properties in hydrocarbons.

E/A particles may be made to have a suitably small size, for example on the order of from about 0.5 micron to about 20 microns or from about 1 to about 10 microns, more preferably from about 1 to about 5 microns, with an excellent particle size distribution, particularly compared to the scattered distribution typically exhibited from polymeric particles prepared by grinding techniques. In addition, E/A particles can have specific surface treatments and shapes depending on the process conditions, which can be important parameters in various end-product uses.

The specific processes of the present invention will now be described in more detail.

In embodiments of the present invention, any suitable polymer material may be used to form the polymeric microspheres. The specific polymer used can depend, for example, on various considerations such as compatibility with the emulsion/aggregation process, compatibility with biological tissue, physical properties such as strength of the particles, chemical properties such as reactivity, and the like. Each of these properties will be readily apparent, or readily determinable, by one of ordinary skill in the art. Illustrative examples of polymer resins selected for the process and particles of the present invention include polyesters such as polyethylene-terephthalate, polypropylene-terephthalate, polybutylene-terephthalate, polypentylene-terephthalate, polyhexalene-terephthalate, polyheptadene-terephthalate, polyoctalene-terephthalate, polyethylene-sebacate, polypropylene sebacate, polybutylene-sebacate, polyethylene-adipate, polypropylene-adipate, polybutylene-adipate, polypentylene-adipate, polyhexalene-adipate, polyheptadene-adipate, polyoctalene-adipate, polyethylene-glutarate, polypropylene-glutarate, polybutylene-glutarate, polypentylene-glutarate, polyhexalene-glutarate, polyheptadene-glutarate, polyoctalene-glutarate polyethylene-pimelate, polypropylene-pimelate, polybutylene-pimelate, polypentylene-pimelate, polyhexalene-pimelate, polyheptadene-pimelate, poly(propoxylated bisphenol-fumarate), poly(propoxylated bisphenol-succinate), poly(propoxylated bisphenol-adipate), poly(propoxylated bisphenol-glutarate), SPAR™ (Dixie Chemicals), BECKOSOL™ (Reichhold Chemical Inc), ARAKOTE™ (Ciba-Geigy Corporation), HETRON™ (Ashland Chemical), PARAPLEX™ (Rohm & Hass), POLYLITE™ (Reichhold Chemical Inc), PLASTHALL™ (Rohm & Hass), CYGAL™ (American Cyanamide), ARMCO™ (Armco Composites), ARPOL™ (Ashland Chemical), CELANEX™ (Celanese Eng), RYNITE™ (DuPont), STYPOL™ (Freeman Chemical Corporation) mixtures thereof and the like, polycarbonates such as LEXAN™ (G.E. Plastics), BAYLON™ (Bayer), MAKROLON™ (Mobay), MERLON™ (Mobay), PANLITE™ (Teijin Chemical), mixtures thereof and like, polyurethanes such as PELLETHANE™ (Dow), ESTANE™ (Goodyear), CYTOR™ (American Cyanamide), TEXIN™ (Mobay), VIBRATHANE™ (Uniroyal Chemical), CONATHANE™ (Conap Company), polystyrene, polyacrylate, polymethacrylate, polystyrene-butadiene, polystyrene-methacrylate, polystyrene-acrylate, mixtures thereof and the like.

According to embodiments of the present invention, suitable polymer materials also include functionalized polymers, i.e., polymers that already incorporate functional groups, which functional groups will in turn be present and available for use in the formed polymeric microspheres. Suitable functionalized polymers thus include, but are not limited to, polystyrene-hydroxyethyl methacrylate, polystyrene-methacrylamide, polystyrene-acrolein, polystyrene-carbohydrate, polymethylmethacrylate-N-methylolacrylamide, polystyrene-4-vinylbenzyl chloride, polystyrene-4-vinylbenzaldehyde, polystyrene-vinylbenzamine, polybutylacrylate-N-(butoxymethyl)acrylamide, polystyrene-butylacrylate-glycidylmethacrylate. Mixtures thereof, and the like. Other suitable functionalized polymers will be apparent to those of ordinary skill in the art, and are equally suitable for use in the present invention.

According to one embodiment of the present invention, an emulsion is prepared by agitating in water a mixture of one or more of an optional nonionic surfactant such as polyethylene glycol or polyoxyethylene glycol nonyl phenyl ether, an optional anionic surfactant such as sodium dodecyl sulfonate or sodium dodecyl benzenesulfonate, and a monomer such as styrene, acrylate, methacrylate, butadiene, butylacrylate, acrylic acid, or isoprene to form polymerized particles. Where more than one monomer is used, or particularly where a monomer or polymer species is used as a seed for the polymerization process, polymerization of the one or more of the monomers or polymers can take place in a manner to encapsulate or otherwise incorporate the monomer or polymer particles by heating from ambient temperature to about 80° C. Emulsion sized resin particles are produced having a volume average diameter of from about 0.02 microns to about 1.2 microns specifically including all suband individual values within the range of about 0.02 microns to about 1.2 microns. The resulting resin emulsion, which typically contains from about 20% to about 60% solids, is then preferably diluted with water to about 15% solids.

Next, one or more optional additives can be added to the resin emulsion, to be incorporated into the desired polymeric particles. For example, suitable additives can include, but are not limited to, colorants, magnetic materials, superparamagnetic materials, bioactive agents, and the like.

For example, one or more colorants, such as pigments or dyes, can be added to the resin emulsion in an amount less than or equal to about 65% by weight of the particle solids and preferably from about 0.5% to about 65% by weight of particle solids. The colorants may be pretreated so as to bind resin particles of the present invention thereto. Alternatively, the colorants may be encapsulated by the resin particles in whole or in part. The resulting mixture may optionally be dispersed utilizing a Brinkman or IKA homogenizer.

Further, for example, one or more bioactive agents, such as medicaments, can be added to the resin emulsion in an amount less than or equal to about 65% by weight of the particle solids and preferably from about 0.5% to about 65% by weight of particle solids. Like the colorants, the bioactive agents may be pretreated so as to bind resin particles of the present invention thereto. Alternatively, the bioactive agents may be encapsulated by the resin particles in whole or in part. The resulting mixture may optionally be dispersed utilizing a Brinkman or IKA homogenizer.

When such additives are incorporated into the resin emulsion, optional flocculation of the emulsion can be conducted to assist in the polymeric microsphere production. When so conducted, a flocculant such as PAC, PASS, amine, cationic salts (such as, for example, magnesium chloride, zinc acetate, calcium chloride, or the like), or cationic surfactant (such as, for example, dialkylbenzene dialkylammonium chloride) and the like is added to effect flocculation of the additives (e.g., colorants, magnetic material, superparamagnetic material, bioactive agents, or the like) with the emulsion resin particles.

The optionally flocculated resin mixture is then suitably homogenized, for example at from about 2000 to about 6000 revolution per minute, to form statically bound aggregate composite particles. The statically bound aggregate composite particles are then heated at a suitable temperature of, for example, from about 60° C. to about 95° C. and for a suitable duration of time of, for example, about 60 minutes to about 600 minutes, to form polymeric particles (microspheres) of the controlled size with narrow size distribution. According to the present invention, the polymeric microspheres can have a suitable volume average diameter (average particle size) of, for example, from about 0.5 micron to about 25 microns, or from about 1 microns to about 15 or about 20 microns, or from about 2 or 3 microns to about 10 or 15 microns. The polymeric microspheres have a geometric standard distribution (GSD) of less than about 1.3, preferably less than about 1.25 or less than about 1.20.

As mentioned above, any suitable monomer or polymer species may be used, as desired. For example, examples of useful monomers that may be included in the monomer latex emulsion prior to polymerization to form latex resin particles include functional monomers such as those described in U.S. Pat. No. 5,853,943, the entire disclosure of which is hereby incorporated by reference in its entirety, and also olefins including, but not limited to, acrylates, acrylic acids, methacrylates, methacrylic acids, acrylonitrile, styrene and its derivatives such as methyl acrylate, ethylacrylate, propyl acrylate, butyl acrylate, hexyl acrylate, methyl methacrylate, ethyl methacrylate, propyl methacrylate, butyl methacrylate, hexyl methacrylate, methyl styrene, and the like. Specific examples of nonionic monomers include styrene, alkyl substituted styrenes, halogenated styrenes, halogenated alkyl substituted styrenes and the like. It is to be understood that other useful monomers will become readily apparent to one of skill in the art based on the present disclosure.

Examples of additional useful monomers include nonionic diolefinic or diene monomers such as butadiene, substituted butadienes, for example, methyl butadiene, isoprene, mycerine, alkyl substituted isoprene, mixtures thereof and the like. It is to be understood that other useful monomers will become readily apparent to one of skill in the art based on the present disclosure.

As desired, and based on the intended use of the polymeric microspheres, one or more monomers or polymers can be used in the polymerization process. When so used, the resultant resin latex can include homopolymers, copolymers, or higher polymers (terpolymers and the like). Where copolymers or terpolymers are present, such polymers can be block, graft, random, or the like, or combinations thereof.

Examples of emulsion resin particles used to form primary polymeric microspheres useful in the present invention include, but are not limited to, poly (styreneacrylate), poly (styrenepoly(styrenemethacrylate), poly(styreneacrylateacid), poly(styreneacid), poly(styrenemethacrylateacid), poly(alkyl methacrylateacrylate), poly (alkyl methacrylateacrylate), poly(aryl methacrylateacrylate), poly(alkyl methacrylateacid), poly(styreneacrylateacid), poly(styreneacid), and poly(alkyl acrylateacid, poly(styrenebutadiene), poly (methylstyrenepoly(methylmethacrylatepoly (ethyl methacrylatepoly(propyl methacrylatepoly(butylmethacrylatepoly(methyl acrylatepoly(ethyl acrylatepoly(propyl acrylatepoly(butyl acrylatepoly(styrenepoly (methylstyrenepoly(methyl methacrylatepoly(ethyl methacrylatepoly(propyl methacrylatepoly(butyl methacrylatepoly(methylacrylatepoly(ethyl acrylatepoly(propyl acrylateand poly(butyl acrylate poly(styreneacrylate), poly(styreneacrylate), poly (styreneacid), poly(styreneacid), poly(styreneacid), poly (styreneacid), poly (styreneacrylateacid), poly(styreneacrylateand poly(styreneacrylateacid) and the like.

Illustrative examples of specific latex resin, polymer or polymers selected for the process of the present invention include known polymers such as poly(styrenepoly (methyl methacrylatepoly(ethyl methacrylatepoly(propyl methacrylatepoly(butyl methacrylatepoly(methyl acrylatepoly(ethylacrylatepoly(propyl acrylatepoly(butyl acrylatepoly(styrenepoly(methylstyrenepoly(methyl methacrylate poly (ethyl methacrylatepoly(propylmethacrylatepoly(butyl methacrylatepoly(methyl acrylatepoly (ethyl acrylatepoly (propyl acrylatepoly(butyl acrylatepoly(styrenepoly(styrenepoly (styrenepoly(styrenemethacrylate), poly(styreneacrylateacid), poly(styreneacid), poly (styreneacid), poly (styrenemethacrylateacid), poly(butyl methacrylateacrylate), poly (butyl methacrylateacid), poly (styreneacrylateacid), poly(acrylonitrileacrylateacid), and the like.

The polymer resins formed from the above mentioned monomers are generally present in the polymeric microspheres in various effective amounts depending, for example, on the amount of the other components, and providing one or more of the objectives of the present invention are achievable. Polymers in the latex resin are generally present in the polymeric microspheres in various effective amounts, such as from about 35 weight percent to about 98 or even to about 100 weight percent of the polymeric microspheres, including all subranges and individual values within the range of from about 35 weight percent to about 98 or even to about 100 weight percent. The latex resin size suitable for the processes of the present invention can be, for example, from about 0.05 microns to about 1.2 microns in volume average diameter as measured by a Brookhaven nanosize particle analyzer or Brookhaven disk centrifuge. Other sizes and effective amounts of latex polymer may be selected in certain embodiments, as desired.

In general, useful colorants or pigments include carbon black, magnetite, or mixtures thereof; cyan, yellow, magenta, or mixtures thereof; or red, green, blue, brown, or mixtures thereof. Typical useful colorants or pigments are present in an effective amount of, for example, from about 1 to about 65 percent by weight, from about 1 to about 25 percent by weight or from about 3 to about 10 percent by weight. Furthermore, in embodiments of the present invention, it may be possible to utilize lesser amounts of the colorants, such as in the range of from about 0.1 to about 10 percent by weight or from about 0.5 to about 5 percent by weight. Specific useful colorants include Paliogen Violet 5100 and 5890 (BASF), Normandy Magenta RD(Paul Uhlich), Permanent Violet VT2645 (Paul Uhlich), Heliogen Green L8730 (BASF); Argyle Green XP(Paul Uhlich), Brilliant Green Toner GR 0991 (Paul Uhlich), Lithol Scarlet D3700 (BASF), Toluidine Red (Aldrich), Scarlet for Thermoplast NSD Red (Aldrich), Lithol Rubine Toner (Paul Uhlich), Lithol Scarlet 4440, NBD 3700 (BASF), Bon Red C (Dominion Color), Royal Brilliant Red RD(Paul Uhlich), Oracet Pink RF (Ciba Geigy), Paliogen Red 3340 and 3871 K (BASF), Lithol Fast Scarlet L4300 (BASF), Heliogen Blue D6840, D7080, K7090, K6910 and L7020 (BASF), Sudan Blue OS (BASF), Neopen Blue FF4012 (BASF), PV Fast Blue B2G01 (American Hoechst), Irgalite Blue BCA (Ciba Geigy), Paliogen Blue 6470 (BASF), Sudan II, III and IV (Matheson, Coleman, Bell), Sudan Orange (Aldrich), Sudan Orange 220 (BASF), Paliogen Orange 3040 (BASF), Ortho Orange OR 2673 (Paul Uhlich), Paliogen Yellow 152 and 1560 (BASF), Lithol Fast Yellow 0991K (BASF), Paliotol Yellow 1840 (BASF), Novaperm Yellow FGL (Hoechst), Permanent Yellow YE 0305 (Paul Uhlich), Lumogen Yellow D0790 (BASF), SucoL1250 (BASF), SucoD1355

(BASF), Sico Fast Yellow D1165, D1355 and D1351 (BASF), Hostaperm Pink E (Hoechst), Fanal Pink D4830 (BASF), Cinquasia Magenta (DuPont), Paliogen Black L0084 (BASF), Pigment Black K801 (BASF) and carbon blacks such as REGAL 330 (Cabot), Carbon Black 5250 and 5750 (Columbian Chemicals), and the like or mixtures thereof.

Additional useful colorants include pigments in water based dispersions such as those commercially available from Sun Chemical, for example SUNSPERSE BHD 6011X (Blue 15 Type), SUNSPERSE BHD 9312X (Pigment Blue 15 74160), SUNSPERSE BHD 6000X (Pigment Blue 15:3 74160), SUNSPERSE GHD 9600X and GHD 6004X (Pigment Green 7 74260), SUNSPERSE QHD 6040X (Pigment Red 122 73915), SUNSPERSE RHD 9668X (Pigment Red 185 12516), SUNSPERSE RHD 9365X and 9504X (Pigment Red 57 15850:1, SUNSPERSE YHD 6005X (Pigment Yellow 83 21108), FLEXIVERSE YFD 4249 (Pigment Yellow 17 21105), SUNSPERSE YHD 6020X and 6045X (Pigment Yellow 74 11741), SUNSPERSE YHD 6001X and 9604X (Pigment Yellow 14 21095), FLEXIVERSE LFD 4343 and LFD 9736 (Pigment Black 7 77226) and the like or mixtures thereof. Other useful water based colorant dispersions commercially available from Clariant include HOSTAFINE Yellow GR, HOSTAFINE Black T and Black TS, HOSTAFINE Blue B2G, HOSTAFINE Rubine 17613 and magenta dry pigment such as Toner Magenta 6BVP2213 and Toner Magenta E02 which can be dispersed in water and/or surfactant prior to use.

Other useful colorants include magnetites, such as Mobay magnetites MO8029, MO8060; Columbian magnetites; MAPICO BLACKS and surface treated magnetites; Pfizer magnetites CB4799, CB5300, CB5600, MCX6369; Bayer magnetites, BAYFERROX 8600, 8610; Northern Pigments magnetites, NPNP Magnox magnetites TMBor TMB the like or mixtures thereof. Specific additional examples of pigments include phthalocyanine HELIOGEN BLUE L6900, D6840, D7080, D7020, PYLAM OIL BLUE, PYLAM OIL YELLOW, PIGMENT BLUE 1 available from Paul Uhlich & Company, Inc., PIGMENT VIOLET 1, PIGMENT RED 48, LEMON CHROME YELLOW DCC 1026, E.D. TOLUIDINE RED and BON RED C available from Dominion Color Corporation, Ltd., Toronto, Ontario, NOVAPERM YELLOW FGL, HOSTAPERM PINK E from Hoechst, and CINQUASIA MAGENTA available from E.I. DuPont de Nemours & Company, and the like. Examples of magentas include, for example, 2,9-dienethylquinacridone and anthraquinone dye identified in the Color Index as CI 60710, CI Dispersed Red 15, diazo dye identified in the Color Index as CI 26050, CI Solvent Red 19, and the like or mixtures thereof. Illustrative examples of cyans include copper tetra(octadecyl sulfonamido) phthalocyanine, xphthalocyanine pigment listed in the Color Index as C174160, CI Pigment Blue, and Anthrathrene Blue, identified in the Color Index as CI 69810, Special Blue X and the like or mixtures thereof; while illustrative examples of yellows that may be selected are diarylide yellow 3,3acetoacetanilides, a monoazo pigment identified in the Color Index as CI 12700, CI Solvent Yellow 16, a nitrophenyl amine sulfonamide identified in the Color Index as Foron Yellow SE/GLN, CI Dispersed Yellow 33 2,5-dienethoxyphenylazoacetoacetanilide, and Permanent Yellow FGL. Colored magnetites, such as mixtures of MAPICO BLACK and cyan components may also be selected as pigments with the process of the present invention. Colorants include pigment, dye, mixtures of pigment and dye, mixtures of pigments, mixtures of dyes, and the like. It is to be understood that other useful colorants will become readily apparent to one of skill in the art based on the present disclosure.

Examples of the surfactant, which can be added to the aggregates before coalescence is initiated, can be anionic surfactants, such as sodium dodecylbenzene sulfonate, sodium dodecylnaphthalene sulfate, dialkyl benzenealkyl, sulfates and sulfonates, abitic acid, available from Aldrich, NEOGEN R, NEOGEN SC obtained from Kao, BIOSOFT D obtained from Stepan, and the like or mixtures thereof. They can also be selected from nonionic surfactants such as polyvinyl alcohol, polyacrylic acid, methalose, methyl cellulose, ethyl cellulose, propyl cellulose, hydroxy ethyl cellulose, carboxy methyl cellulose, polyoxyethylene cetyl ether, polyoxyethylene lauryl ether, polyoxyethylene octyl ether, polyoxyethylene octylphenyl ether, polyoxyethylene oleyl ether, polyoxyethylene sorbitan monolaurate, polyoxyethylene stearyl ether, polyoxyethylenenonylphenyl ether, dialkylphenoxypoly(ethyleneoxy) ethanol, available from Rhoneas IGEPAL CAIGEPAL CAIGEPAL CAIGEPAL COIGEPAL COIGEPAL COIGEPAL CAANTAROX 890, ANTAROX 897, and the like or mixtures thereof. An effective amount of the anionic or nonionic surfactant utilized in the coalescence to primarily stabilize the aggregate size against further growth with temperature is, for example, from about 0.01 to about 10 percent by weight, and preferably from about 0.5 to about 5 percent by weight of the reaction. Additional methods of stabilizing aggregate size include raising pH of the emulsion above 6, such as through the addition of sodium hydroxide or potassium hydroxide.

Dyes that are invisible to the naked eye but detectable when exposed to radiation outside the visible wavelength range (such as ultraviolet or infrared radiation), such as dansylN-(2-aminoethyl)-4-amino-3,6-disulfo-1,8-dinaphthalimide dipotassium salt, N-(2-aminopentyl)-4-amino-3,6-disulfo-1,8-dinaphthalimide dipotassium salt, Cascade Blue ethylenediamine trisodium salt (available from Molecular Proes, Inc.), Cascade Blue cadaverine trisodium salt (available from Molecular Proes, Inc.), bisdiazinyl derivatives of 4,4'-diaminostilbene-2,2'-disulfonic acid, amide derivatives of 4,4'-diaminostilbene-2,2'-disulfonic acid, phenylurea derivatives of 4,4'-disubstituted stilbene-2,2'-disulfonic acid, mono- or di-naphthyltriazole derivatives of 4,4'-disubstituted stilbene disulfonic acid, derivatives of benzithiazole, derivatives of benzoxazole, derivatives of benzimidazole, derivatives of coumarin, derivatives of pyrazolines containing sulfonic acid groups, 4,4'-bis(triazin-2-ylamino)stilbene-2,2'-disulfonic acids, 2-(stilben-4-yl)naphthotriazoles, 2-(4-phenylstilben-4-yl) benzoxazoles, 4,4-bis(triazo-2-yl) stilbene-2,2'-disulfonic acids, 1,4-bis(styryl) biphenyls, 1,3-diphenyl-2-pyrazolines, bis(benzazol-2-yl) derivatives, 3-phenyl-7(triazin-2-yl)coumarins, carbostyrils, naphthalimides, 3,7-diaminodibenzothiophen-2,8-disulfonic acid-5, 5-dioxide, other commercially available materials, such as C.I. Fluorescent Brightener No. 28 (C.I. 40622), the fluorescent series Leucophor BBMB (C.I. 290), BCR, BS, and the like (available from Leucophor), and the like, are also suitable.

In addition, suitable colorants that can be used in the present invention can include one or more fluorescent colorants, which can be pigments, dyes, or a mixture of pigments and dyes. For example, suitable fluorescent pigment concentrates are disclosed in, for example, U.S. Pat. No. 4,911,830, the entire disclosure of which is incorporated herein by reference, and suitable fluorescent colorants are disclosed in, for example, U.S. Pat. Nos. 4,243,694 and 5,554,480, the entire disclosures of which are incorporated herein by reference. Suitable inorganic fluorescent pigments can be prepared, for example, by adding trace amounts of activating agents such as copper, silver and manganese to high purity sulfides of heavy metals or alkaline earth metals such as zinc sulfide, which are used as raw materials, and calcining them at a high temperature. Suitable organic fluorescent pigments can be prepared, for example, by dissolving fluorescent dyes in the vehicles of synthetic resins or ones prepared by dyeing the dispersed matters of fine resin particles obtained by emulsion polymerization or suspension polymerization with fluorescent dyes. The synthetic resins can include, but are not limited to, vinyl chloride resins, alkyd resins and acrylic resins, and the fluorescent dyes include, but are not limited to, C.I. acid yellow 7, C.I. basic red 1 and the like.

Although not limited thereto, suitable fluorescent dyes include, but are not limited to, those belonging to the dye families known as rhodamines, fluorsciens, coumarins, napthalimides, benzoxanthenes, acridines, azos, and the like. Suitable fluorescent dyes include, for example, Basic Yellow 40, Basic Red 1, Basic Violet 11, Basic Violet 10, Basic Violet 16, Acid Yellow 73, Acid Yellow 184, Acid Red 50, Acid Red 52, Solvent Yellow 44, Solvent Yellow 131, Solvent Yellow 85, Solvent Yellow 135, solvent Yellow 43, Solvent Yellow 160 and Fluorescent Brightener 61. Suitable fluorescent pigments include, but are not limited to, those available from Day-Glo Color Corp. of Cleveland, Ohio, such as aurora pink T-11 and GT-11, neon red T-12, rocket red T-13 or GT-13, fire orange T-14 or GT-14N, blaze orange T-15 or GT-15N, arc yellow T-16, saturn yellow T-17N, corona magenta GT-21 and GT-17N, and the like.

As mentioned above, magnetic and/or superparamagnetic materials can also be incorporated in the polymeric microspheres. Such magnetic materials can be included, for example, to give the polymeric microspheres magnetic and/or superparamagnetic properties, for colorant properties, or the like. Suitable magnetic and/or superparamagnetic materials that can be used in the present invention include, but are not limited to, magnetites, ferrites, and the like. Examples of suitable magnetites, in addition to the magnetites mentioned above, include, but are not limited to, a mixture of iron oxides (FeO, $Fe_2O_3$), including those commercially available as MAPICO BLACK™. Other examples of suitable magnetic materials include, but are not limited to, barium ferrite powder ($BaO.6Fe_2O_3$), strontium ferrite powder ($SrO.6Fe_2O_3$), barium-strontium ferrite powder ($Ba_xSr_{1-x}O.6Fe_2O_3$), $SmCo_5$-based based powder, $Sm_2Co_{17}$-based powder, $Nd_2Fe_{14}B$-based powder, $Sm_2Fe_{17}N_3$-based powder, $(NdDy)_{15}Fe_{79}B_6$, alloys of 33Ne 66Fe 1B, an Nd—Fe—B-based quenched magnetic powder (such as the product MQP-B manufactured by GM), ferrite particles, and the like. Examples of suitable ferrites include, but are not limited to, ferrites such as MnZn ferrite and NiZn ferrite. Any other suitable magnetic and/or superparamagnetic material can also be used. The magnetic and/or superparamagnetic material can be present in the polymeric microspheres in any of various effective amounts, such as an amount of from about 10 percent by weight to about 75 percent by weight of the polymeric microspheres. Preferably, the magnetite and/or superparamagnetic is present in an amount of from about 30 percent to about 55 percent by weight of the polymeric microspheres.

Examples of suitable flocculants or cationic surfactants that can be included in the processes of the present invention include, for example, but are not limited to, dialkyl benzenealkyl ammonium chloride, lauryl trimethyl ammonium chloride, alkylbenzyl methyl ammonium chloride, alkyl benzyl dimethyl ammonium bromide, benzalkonium chloride, cetyl pyridinium bromide, CCCtrimethyl ammonium bromides, halide salts of quaternized polyoxyethylalkylamines, dodecylbenzyl triethyl ammonium chloride, MIRAPOL ALKAQUAT available from Alkaril Chemical Company, SANIZOL (benzalkonium chloride), available from Kao Chemicals, polyaluminum chloride (PAC), polyaluminum sulfate silicate (PASS), cationic salts (such as, for example, magnesium chloride, zinc acetate, calcium chloride, or the like), and the like, whether alone or in combination or mixture with other flocculants or cationic surfactants. Such flocculants or cationic surfactants can be included in effective amounts of, for example, from about 0.01 percent to about 10 percent by weight. Preferably, the molar ratio of the cationic surfactant used for flocculation to the anionic surfactant used in the latex preparation is in the range of from about 0.5 to 4. It is to be understood that other useful anionic and cationic surfactants will become readily apparent to one of skill in the art based on the present disclosure.

Examples of useful chain transfer agents that can be included in the processes of the present invention include, for example, but are not limited to, dodecanethiol, carbon tetrabromide and the like, which can be used to control the molecular weight properties of the polymer when emulsion polymerization is carried out. It is to be understood that other useful chain transfer agents will become readily apparent to one of skill in the art based on the present disclosure. An effective concentration of a chain transfer agent that is generally employed is, for example, from about 0.005 to about 10 percent by weight, or from about 0.01 to about 5 percent by weight, or from about 0.1 to about 3 percent by weight.

Examples of useful optional free radical initiators that can be selected for the preparation of the polymeric microspheres include azoinitiators such as 2azobis (isobutyronitrile), azobis(cyclohexaneazobis(methylmixtures thereof, and the like, peroxide initiators such as benzoyl peroxide, lauroyl peroxide, methyl ethyl ketone peroxide, isopropyl peroxy2,5-dienethyl-2,5-bas(2-ethylhexanoyl-peroxy)hexane, diperoxide, cumene hydroperoxide, dichlorobenzoyl peroxide, potassium persulfate, ammonium persulfate, sodium bisulfate, combination of potassium persulfate, sodium bisulfate and the like, and mixtures thereof. It is to be understood that other useful free radical initiators will become readily apparent to one of skill in the art based on the present disclosure. An effective quantity of an initiator is generally within the range of about 0.1 percent to about 10 percent by weight of the reaction mixture.

In addition to the above specifically identified monomers and polymers, the processes of the present invention are also applicable to polymeric microspheres made from polyester resins, such as sulfonated polyester resins. In these embodiments, the emulsion./aggregation process can proceed using the processes and materials as generally described in U.S. Pat. Nos. 5,348,832, 5,593,807, 5,604,706, 5,853,944, 5,919,595, and 5,945,245, the entire disclosure of which is incorporated herein by reference.

In such polyester emulsion/aggregation processes, the polyester can generally be obtained from the melt esterification of at least one dicarboxylic acid or diester components with at least one diol component, and optionally a sulfonated difunctional monomer, and using a polycondensation catalyst. Of course, the polyester can be formed from multiple types of one or more of the components, i.e., can be formed using more than one dicarboxylic acid or diester component (such as one to ten, preferably one to two), and/or more than one diol component (such as one or two). The dicarboxylic acid and/or diester components are generally present in an amount of from about 42 mole percent to about 49.5 mole percent of the polyester; the diol component is generally present in an amount of about 50 mole percent of the polyester resin; and the sulfonated difunctional monomer, when present, is generally present in an amount of from about 0.5 to about 8 mole percent of polyester. The polycondensation catalyst is generally present in an amount of from about 0.01 to about 0.1 mole percent of the polyester. Examples of suitable dicarboxylic acid or diester components include dimethyl terephthalate and isophthalic acid; examples of suitable diol components include 1,2-propylene glycol, and propoxylated bisphenol A diethylene glycol; and examples of sulfonated difunctional monomers include dimethyl-5-sulfo-isophthalate sodium salt, and sodium 2-sulfophthalic anhydride. Suitable polycondensation catalyst include, for example, dibutyl tin oxide hydroxide.

The emulsion/aggregation process for forming such polyester polymeric microspheres generally comprises the steps of obtaining or forming the polyester resin, followed by (a) dissipating the polyester resin in water by heating at from about 60° C. to about 120° C. with mixing for a duration of from about 1 minute to about 1 hour thereby generating suspended polyester particles of from about 0.01 micron to about 2 microns in average particle diameter; (b) subsequently adding to the resulting emulsion suspension an optional pigment or other additive dispersion, such as in an aqueous mixture containing a counterionic metal salt, and resulting in the aggregation and coalescence of resin particles and optional pigment or additive of from about 3 to about 21 microns thereby providing polymeric microspheres with a desired average particle volume diameter; and (c) cooling the mixture to ambient temperature, about 25° C., washing with water from about three to about six times, and drying the product by known methods such as fluid bed dryer.

Although the various polyester components are not particularly limited, examples of suitable diol, diester, and the like components are set forth below. However, it will be apparent to those skilled in the art that other materials may be used.

Specific examples of the diol component suitable for use in the present invention include, but are not limited to, ethylene glycol, 1,2-propylene glycol, 1,3-propylene glycol, 1,2-butylene glycol, 1,3-butylene glycol, 1,4-butylene glycol, 1,2-pentylene glycol, 1,3-pentylene glycol, 1,4-pentylene glycol, 1,5-pentylene glycol, 1,2-hexylene glycol, 1,3-hexylene glycol, 1,4-hexylene glycol, 1,5-hexylene glycol, 1,6-hexylene glycol, heptylene glycols, octylene glycols, decylne glycol, dodecylyne glycol, 2,2-dimethyl propane diol, propoxylated bisphenol A, ethoxylated bisphenol A, 1,4-cyclohexane diol, 1,3-cyclohexane diol, 1,2-cyclohexane diol, 1,2-cyclohexane dimethanol, 2-propene-diol, mixtures thereof, and the like. Such diols can be employed in any suitable and effective amount of, for example, from about 45 to about 55 mole percent by weight of the resin.

Specific examples of dicarboxylic acid component suitable for use in the present invention include, but are not limited to, malonic acid, succinic acid, 2-methyl succinic acid, 2,3-dimethylsuccinic acid, dodecylsuccinic acid, glutaric acid, adipic acid, 2-methyladipic acid, pimelic acid, azeilic acid, sebacic acid, terephthalic acid, isophthalic acid, phthalic acid, 1,2-cyclohexanedioic acid, 1,3-cyclohexanedioic acid, 1,4-cyclohexanedioic acid, glutaric anhydride, succinic anhydride, dodecylsuccinic anhydride, mixtures thereof, and the like. Such dicarboxylic acids can be used in any suitable and effective amount of, for example, from about 45 to about 55 mole percent by weight of the resin.

Specific examples of dicarboxylic diesters suitable for use in the present invention include, but are not limited to, alkyl esters, wherein the alkyl groups contain from 1 to about 23 carbons and are esters of malonate, succinate, 2-methyl succinate 2,3-dimethyl succinate, dodecyl succinate, glutarate, adipic acid, 2-methyladipate, pimelate, azeilate, sebacate acid, terephthalate, isophthalate, phthalate, 1,2-cyclohexanedioate, 1,3-cyclohexanedioate, 1,4-cyclohexanedioate, mixture thereof, and the like. Such diesters can be used in any suitable and effective amount of, for example, from about 45 to about 55 mole percent by weight of the resin.

Specific examples of sulfonated difunctional monomers suitable for use in the present invention include, but are not limited to, the ion salts of sulfonated difunctional monomers wherein the ion is a hydrogen, ammonium, an alkali or alkaline earth such as lithium, sodium, potassium, cesium, magnesium, barium, or a metal ion such as vanadium, copper, iron cobalt, manganese, mixtures thereof and the like, and the sulfonated difunctional moiety is selected from the group including dimethyl-5-sulfo-isophthalate, dialkyl-5-sulfo-isophthalate-4-sulfo-1,8-naphthalic anhydride, 4-sulfo-phthalic acid, dimethyl 4-sulfo-phthalate, dialkyl 4-sulfo-phthalate, 4-sulfophenyl-3,5-dicarbomethoxybenzene, 6-sulfo-2-naphthyl-3,5-dicarbomethoxybenzene, sulfo-terephthalic acid, dimethyl-sulfo-terephthalate, dialkyl-sulfo-terephthalate, sulfo-ethanediol, 2-sulfopropanediol, 2-sulfobutanediol, 3-sulfopentanediol, 2-sulfo hexanediol, 3-sulfo-2-methylpentanediol, 2-sulfo-3,3-dimethylpentanediol, sulfo-p-hydroxybenzoic acid, mixtures thereof, and the like. Such difunctional compounds can be used in an amount of, for example, from about 0.5 to about 8 mole percent by weight of the resin. Two preferred monomers are dimethyl-5-sulfo-isophthalate sodium salt, and N,N-bis(2-hydroxyethyl)-2-aminoethane sulfonate available as BES from Aldrich Chemical Company.

Surfactants suitable for use in the polyester process include those surfactants specified above.

Specific examples of polycondensation catalysts suitable for use in the present invention include, but are not limited to, tetraalkyl titanates, dialkyltin oxide, tetraalkyltin, dialkyltin oxide hydroxide, aluminum alkoxides, alkyl zinc, dialkyl zinc, zinc oxide, stannous oxide, dibutyltin oxide, butyltin oxide hydroxide, tetraalkyl tin such as dibutyltin dilaurate, mixtures thereof, and the like. Such catalysts can be used in any suitable and effective amount of from about 0.01 mole percent to about 1 mole percent of resin.

Specific examples of sulfonated polyesters formed from the above process include, but are not limited to, the hydrogen, ammonium, alkali or alkali earth metals such as lithium, sodium, potassium, cesium, magnesium, barium, iron, copper, vanadium, cobalt, calcium of the random copoly(ethylene-terephthalate)-copoly-(ethylene-5-sulfo-isophthalate), copoly(propylene-terephthalate)-copoly-(propylene-5-sulfo-isophthalate), copoly(diethylene-terephthalate)-copoly-(diethylene-5-sulfo-isophthalate), copoly (propylene-diethylene-terephthalate)-copoly(propylene-diethylene-5-sulfo-isophthalate), copoly(propylene-butylene-terephthalate)-copoly-(propylene-butylene-5-sulfo-isophthalate), copoly-(propoxylated bisphenol-A-fumarate)-copoly(propoxylated bisphenol A-5-sulfo-isophthalate), copoly (ethoxylated bisphenol-A-fumarate)-copoly(ethoxylated bisphenol A-5-sulfo-isophthalate), copoly(ethoxylated bisphenol-A-maleate)-copoly(ethoxylated bisphenol A-5-sulfo-isophthalate), mixtures thereof and the like, and wherein the sulfonated copoly portion is present in an amount of, for example, from about 0.5 to about 8 mole percent of the resin. For the aforementioned sulfonated polyester resins, the glass transition temperature can be selected to be from about 45° C. to about 65° C. as measured by the Differential Scanning Calorimeter, the number average molecular weight can be selected to be from about 2,000 grams per mole to about 150,000 grams per mole, the weight average molecular weight can be selected to be from about 3,000 grams per mole to about 300,000 grams per mole as measured by the Gel Permeation Chromatograph, and the polydispersity can be selected to be from about 1.6 to about 100 as calculated by the ratio of the weight average to number average molecular weight.

If desired for the particular applications of the polymeric microspheres, the polymeric microspheres may also optionally include known charge additives in effective suitable amounts of, for example, from 0.1 to 5 weight percent. Such charge additives are well known for use in electrostatographic imaging toner compositions. Examples of such charge additives, include, but are not limited to, alkyl pyridinium halides, bisulfates, the charge control additives of U.S. Pat. Nos. 3,944,493; 4,007,293; 4,079,014; 4,394,430 and 4,560,635, which illustrates a toner with a distearyl dimethyl ammonium methyl sulfate charge additive, the entire disclosures of which are totally incorporated herein by reference, as well as negative charge enhancing additives such as aluminum complexes, and the like.

Once the polymeric microspheres are formed, they can be isolated from the reaction mixture by any suitable means. Suitable isolation methods include, but are not limited to, filtration, particle classification, and the like.

Alternatively, the formed polymeric microspheres can optionally be washed and dried by conventional means. For example, the formed polymeric microspheres can be washed using, for example, water, preferably deionized water, or other suitable materials. The formed polymeric microspheres can likewise be dried using, for example, a heated drying oven or the like.

Following the optional particle classification, washing and/or drying, the particles may be subjected to an optional chemical surface treatment. For example, the polymeric particles may be subjected to any desirable surface treatment to alter the chemical and/or physical properties of the particle, such as hydrophobicity, hydrophilicity, surface charge, and the like, or to attach or alter functional groups present on the surface of the microspheres.

Surface additives that can optionally be added to the polymeric microspheres after washing or drying include, for example, metal salts, metal salts of fatty acids, colloidal silicas, metal oxides like titanium oxides such as STT 10011 commercially available from Carboxil, mixtures thereof and the like, which additives are usually present in an amount of from about 0.1 to about 2 weight percent, reference U.S. Pat. Nos. 3,590,000; 3,720,617; 3,655,374 and 3,983,045, the disclosures of which are totally incorporated herein by reference. Additional additives include zinc stearate in an amount of from about 0.1 percent to about 2% and silica such as AEROSIL R972.R, RX50, 7095, T681IS, TG81 0S, TG308S, S530 and TS720 available from Degussa in amounts of from about 0.1 to about 5 percent which can be added during the aggregation process or blended into the formed product.

The formed polymeric microspheres of the present invention can also or alternatively be surface halogenated, partially or wholly, for example 100 percent, to convert olefinic double bonds by an electrophilic addition reaction in the surface polymer chain backbone and pendant groups into the corresponding halogenated hydrocarbon functionality. In many instances, surface halogenation of the polymeric microspheres affords further control of the variety of rheological properties that may be obtained from the copolymer resins. Surface halogenation is accomplished with a gaseous mixture or liquid solution of an effective amount of from 0.01 to about 5 double bond molar equivalents of halogen gas or halogen liquid dissolved in water, or an organic solvent, for example, chlorine gas, liquid bromine, or crystalline iodine dissolved in a solvent, such as an aliphatic alcohol, like ethanol which does not dissolve or substantially alter the size or shape of the polymeric microspheres.

When more reactive halogens such as fluorine are used, an inert carrier gas, such as argon or nitrogen, may be selected as a diluent, for example, from about 0.1 to about 98 percent by volume of the inert gas relative to the reactive halogen gas, to moderate the extent of reaction, and the temperature and control corrosivity of the halogenation process.

A number of equally useful halogenating agents are known that afford equivalent reaction products with olefinic double bonds as the aforementioned diatomic halogens, for example as disclosed by House in "Modern Synthetic Reactions", W. A. Benjamin, Inc., $2^{nd}$ Ed., Chapter 8, page 422, and references cited therein, the disclosure of which is incorporated in its entirety by reference.

The aforementioned halogenation can be considered an addition reaction. That is, for example, the halogen reacts with, and diffuses into the polymer resin, whereby a shell thereof is formed. The shell can be of various effective thicknesses; generally, however, the shell is of a thickness of from about 1 micron or less, and more specifically from about 0.1 to about 1 micron, in embodiments. Typical amounts of halogen consumed include, for example, from about 0.1 to about 1 gram of halogen per 100 grams of polymer resin.

Numerous other functional groups can be present on the surface of the polymeric microspheres, either by virtue of them being present in the polymer material itself resulting from the polymerization process, or by means of surface modification of the formed microspheres. Various methods for forming such surface functional groups are known in the art, and will be apparent based on the present disclosure. Such functional groups already present on the surface of the microsphere or formed thereafter can be modified to enable ready attachment of biological or other materials. Alternatively, or in addition, the functional groups can be reacted with materials that in turn may act as linkages to biological materials, ligands or other materials.

By way of example, only, hydroxyl groups can be reacted with sulfonyl chlorides to enable nucloeophilic attack by amines, alcohols, and the like. For example, the amine portion of a protein can react and lead to attachment of the protein to the surface of the microsphere. Alcohols can also undergo esterification to attach reactive functional groups, to which biological or other materials can be readily attached. Primary amines can be converted to amides, acids, or sulfonates, which can possess suitable functional groups for further manipulation. Chloromethyl groups can be converted to amines, ethers, aldehydes and thiols, each of which can be readily linked to biological or other materials by known methods. Carboxylic acid can be converted to esters or amides and can often directly react with proteins. Ester groups can undergo transesterification. Amino groups can couple to proteins with glutaraldehyde. Epoxy groups introduced by any of the previous manipulations (or others) can be readily reacted with biological materials to enable attachment. Other types of surface treatments suitable for use according to the present invention include making the particles more hydrophobic through the complexation of surface functional groups such as sulfonates with quaternary ammonium salts (or other cationic salts) to mask the hydrophilic groups.

Other surface treatments or modifications suitable for use in the present invention include, but are not limited to, such modification and treatments as disclosed in U.S. Pat. Nos. 5,869,216, 5,902,710, 6,143,457, the entire disclosures of which are incorporated herein by reference.

Of course, two or more different surface treatments or modifications can be performed on the same microsphere, if desired. Such multiple surface treatment or modification can be advantageous, for example, to enable attachment of multiple different materials or to provide multiple functionalities to the microspheres.

The polymeric microspheres prepared according to the processes of the present invention can be used for a variety of uses. While not being limited to any particular uses, the microspheres are especially useful for biological and medical purposes. Accordingly, the polymeric microspheres of the present invention, including any additives incorporated therein or thereon, are preferably biocompatible. By biocompatible herein is meant that the polymeric microspheres and additives are not destructive to healthy living tissues, at least beyond any desired effect for which the polymeric microspheres are intended, over the lifetime that the polymeric microspheres are in contact with or proximity to such biological tissues.

Of course, it is not necessary in all embodiments of the present invention for the polymeric microspheres to be biocompatible. Thus, for example, where the polymeric microspheres are to be used ex vivo, such as in laboratory experiments, assays, or the like, biocompatibility is unnecessary.

The microspheres described herein can be used as size standards for analytical purposes. Such a use of microspheres or microparticles is well-known to those of skill in the art.

In a preferred embodiment of the invention, the microspheres are composed of biodegradable, biocompatible polymers and contain a bioactive agent dispersed therein. The bioactive agent may be dissolved within the polymer phase or dispersed as discrete solid particles.

Microspheres of the present invention can also be used for embolization. For example, microsphere-induced embolization has been used to treat vascular disease (see, for example, Beaujeux et al., Am. J. Neuroradiol. 17:541 (1996)). Moreover, microspheres have been used for preoperative embolization of hemangioblastomas (see, for example, Eskridge et al., Am. J. Neuroradiol. 17:525 (1996)).

The present invention also contemplates the use of microspheres to measure the rate of blood flow. As an illustration, Young et al., Urol. Res. 24:149 (1996), used a microsphere technique for visual assessment of renal blood flow.

Uniformly sized microspheres can also be used to deliver a bioactive agent to a subject in need of treatment. Such therapeutic microspheres can be produced either by incorporating a bioactive drug within the microspheres, or by binding a bioactive drug to the surfaces of microspheres. Examples of suitable bioactive agents include anti-proliferative agents, steroids, analgesics, narcotic antagonists, antibiotics, anti-fungals, anti-histamines, anti-asthmatics, beta-blockers, and anti-cancer agents. In addition, radioactively-labeled microspheres can be used for therapeutic purposes. As an illustration, 90-yttrium has been used to treat hepatic tumors (see, for example, Leung et al., Int. J. Radiat. Oncol. Biol. Phys. 33:919 (1995), and Ho et al., Eur. J Nucl. Med. 24:293 (1997)).

A suitable bioactive agent for incorporation within a microsphere should have a solubility parameter close to that of the polymer used to make the microsphere. In this way, the same solvent can be used to dissolve the bioactive agent and the polymer to produce a homogeneous solution.

Such a preference for solubility does not apply, however, to therapeutic microspheres comprising a bioactive agent bound to the surface. For example, polypeptides, such as pharmacologically active peptides, antigens, and antibodies, are suitable for binding to microsphere surfaces. As an illustration, microspheres can be produced that bear an infectious agent antigen for vaccination.

Microspheres can also be produced that comprise bioactive agents incorporated within the microsphere and bound to the surface. For example, antibodies or antibody fragments can be bound to a microsphere surface to target delivery of another bioactive agent contained within the microsphere.

In addition, microspheres can be incorporated into a second polymer. That is, uniformly sized microspheres can be dispersed throughout a gel or a viscous solution, or dispersed throughout a solid, biodegradable polymer scaffold.

Therapeutic microspheres can be delivered to a subject via transdermal, oral, nasal, pulmonary, ocular, or parenteral routes. Examples of parenteral routes include intramuscular, intra-tumoral, intra-arterial, and intravenous administration. Since therapeutic microspheres can be used for both human therapy and veterinary purposes, suitable subjects include both humans and non-human animals.

Microspheres comprising a bioactive agent can also be used in a variety of agricultural applications.

Controlled release systems for the release of macromolecules from a polymer matrix have been proven effective for many applications. Since 1971, poly(ethylene vinylacetate), (EVA) has been studied for this use, and EVA may be used as the polymer in the compositions according to the processes described above. EVA is a hydrophobic, non-degradable polymer that has proven biocompatibility. It has been used in delivery systems for various macromolecules such as herapin, enzymes, and antigens. The mechanism of controlled release of macromolecules from non-degradable polymers has been shown to involve aqueous diffusion of the macromolecule through a network of interconnecting channels that arise within the polymer at the time of incorporation of the macromolecule.

Recent work has demonstrated the controlled release of angiogenic and angiostatic proteins from an EVA matrix. The release of angiostatic proteins might find application in treating certain forms of cancer. The treatment would proceed by delivering angiostatic proteins to a tumor site thus inhibiting the circulation of blood to the tumor. The delivery of this drug, through the blood stream to such a location is well suited to employing microspheres as the drug carrier. Microspheres appear themselves to significantly block blood flow in capillary beds, and microspheres containing chemotherapeutic drugs have been used in treating developed tumors.

To achieve such uses, the polymeric microspheres of the present invention can be processed to attach suitable and desirable biological or medical materials to the surfaces of the microspheres. Such biological or medical materials include materials that serve specific therapeutic, diagnostic, analytical, or experimental purposes and include, but are not limited to, radioactive, biological, and ligand materials. The biological or medical materials can be attached to the surface of the microspheres by, for example, covalent bonding, complexation, physical adsorption, physical absorption, and the like.

In the case of radio-labeled or radioactive polymeric microspheres, the radioactive component can be incorporated into the microsphere or can be applied to the formed microsphere, as desired. When incorporated into the microsphere itself, it is appropriate to add the radioactive material to the emulsion during the production process. The radioactive component can, as desired, be a material that is itself radioactive, or it can be a radioactive precursor material that becomes radioactive upon exposure to a suitable initiating source.

In a preferred embodiment of the present invention, the radioactive constituent of the microspheres is chosen so that when administered to the patient, the radioactive microspheres emit a therapeutic intensity and amount of short-range (e.g., a penetration of the tissue on the order of about several millimeters or less) beta or gamma radiation, but will not emit a significant amount of unwanted beta or gamma radiation that could have a negative impact on healthy tissue surrounding the cancerous or tumor bearing tissue. In this regard, it is preferred that the components of the polymeric microspheres be selected so that the radiation emitting radioisotopes are the only constituent isotopes that may emit a significant amount of radiation beyond a relatively short period of time, e.g., on the order of about 1 week or less. Elements such as yttrium and phosphorus, which form radioisotopes having a half-life greater than about two days and less than about 30 days, are particularly preferred as the elements that emit therapeutic radiation. The balance of the constituent elements of the polymeric microspheres, i.e., polymer and other additives, are preferably selected so that when administered, the microsphere does not emit any significant amount of radiation other than that emitted by Y-90 or P-32. This result may be accomplished by selecting a composition that contains yttrium-89 or phosphorus-31 and a balance of elements that either do not become radioactive during neutron irradiation or that have a sufficiently short half-life so as not to emit a significant amount of beta or gamma radiation at the time of administration.

In accordance with the present invention, the radioisotope component of the polymeric microspheres may be chosen so that the radiation may be tailored to deliver a radiation profile that is ideally suited for a particular treatment. For instance, in some instances it may be preferred to employ a radiotherapeutic product with short-lived beta emitter Y-90, while in others it may be preferred to utilize the longer-lived beta emitter P-32 or a product that has both components. In other instances, it may be desirable to employ a radiotherapeutic product with a gamma emitting isotope or a mixture of beta and gamma emitting isotopes. In a preferred embodiment, a beta emitter and/or a low energy gamma emitting nuclide is incorporated into the microspheres. In another preferred embodiment, yttrium and/or phosphorus are incorporated into the microspheres; where P-32 emits pure beta radiation and Y-90 emits nearly pure beta radiation that will spare healthy tissue remote from the tumor site in which the microsphere is embedded.

The remaining constituent elements of the polymeric microspheres of the present invention are also preferably chosen so that the microsphere does not contain any significant amount of elements that have a large cross-section for neutrons. An example of one such element that has a large cross-section for neutrons is boron, which has a cross-section of 3837 barns. In a most preferred embodiment, the microspheres do not contain a significant amount of any elements that have a cross-section for neutrons greater than about 200 barns.

The radiation dosage delivered through the use of the activated microspheres upon administration to a patient can be varied by controlling the number of microspheres administered and by controlling the amount of radiation emitting isotopes contained by the microspheres. The amount of radiation emitting isotopes contained by the microspheres is affected by two factors: the amount of the stable element that will be converted to a radioelement by irradiation, and the length of time of irradiation. Preferably, the microspheres are irradiated for a short period of time with an intense thermal neutron flux generated by a nuclear fission reactor instead of being irradiated for a significantly longer period of time with a lesser neutron flux. This technique of a short, intense irradiation of the microsphere is particularly preferred where one or more of the constituent elements of the microsphere has an undesired radiation profile and a half-life that is significantly greater than those constituent elements having a desired radiation profile. Thus, the manner of irradiation may be controlled in such a manner to impart the microsphere with a therapeutic intensity and amount of radiation while also minimizing the amount of undesired radiation.

In the case of polymeric microspheres containing a biological material, one or more biological materials can be incorporated into the microsphere or can be applied to the formed microsphere, as desired. When incorporated into the microsphere itself, it is appropriate to add the bioactive material to the emulsion during the production process.

As used herein, a bioactive material, or bioactive agent, refers to materials that exhibit therapeutic effects when applied or otherwise exposed to biological tissues, organs, fluids or the like. Bioactive materials, or bioactive agents, thus refers to any such materials that include medicaments, as well as other active agents that effect such biological tissues, organs, fluids or the like.

Examples of such bioactive materials thus include, but are not limited to, antibiotics, antimicrobials, antiseptics, bacteriocins, bacteriostats, disinfectants, steroids, anesthetics, fungicides, anti-inflammatory agents, antibacterial agents, antiviral agents, antitumor agents, growth promoters, and mixtures thereof. Preferable bioactive materials are USP approved, more preferably USP monographed.

Likewise, in the case of polymeric microspheres including one or more ligands, ligand can be incorporated into the microsphere or can be applied to the formed microsphere, as desired. Preferably, when ligands are to be included in or on the microspheres, the ligand can be added to the material to the emulsion during the production process, but it is preferably instead added onto the surface of the microspheres after the microspheres are formed.

Suitable ligands that can be attached to the polymeric microspheres according to the present invention include any of the known or after-developed ligands, in known amounts for their known purposes. Thus, for example, suitable ligands include, but are not limited to, proteins, enzymes, analytes, antigens, antibodies, and the like. Such materials can be attached to the microsphere surface, such as through absorption or adsorption, as disclosed in U.S. Pat. No. 6,207,171, the entire disclosure of which is incorporated herein by reference.

Suitable antigen may be derived from a cell, bacterium, virus particle, or a portion thereof. The antigen may be a protein, peptide, polysaccharide, glycoprotein, glycolipid, nucleic acid, or a combination thereof, which elicits an immune response in an animal, including mammals, birds, and fish. The immune response may be a humoral immune response or a cell-mediated immune response. In the event the material to which the immune response is to be directed is poorly antigenic, it may be conjugated to a carrier such as albumin or to a hapten, using standard covalent binding techniques, for example, with one of the several commercially available reagent kits. In some embodiments it may be desirable to include an additional adjuvant with the antigen. Of course, other suitable antigens could also be used, and the present invention is not limited to any specific type.

Examples of preferred antigens include viral proteins such as influenza proteins, human immunodeficiency virus HIV proteins, Haemophilus influenza proteins, hepatitis B proteins, and bacterial proteins and lipopolysaccharides such as gram negative bacterial cell walls and Neisseria gonorrhea proteins.

The polymeric microspheres of the present invention may be solid, hollow, or porous, as desired. Thus, for example, the polymeric microspheres may be essentially void-free (solid) microspheres, or may be microshells, i.e., microspheres having a hollow core. Alternatively, the microspheres may have a "foam-like" structure where the microsphere has a plurality of hollow cells. Microshells and microspheres having a plurality of hollow cells may be preferred where it is desired to employ a microsphere having a density substantially less than that of the essentially void-free microsphere.

Whether the microspheres of the present invention are essentially void-free, microshells, or have a plurality of hollow cells, it is preferred that the microspheres be substantially spherical, i.e., there are no sharp edges or points that would cause the microsphere to lodge in a location other than that desired. In this context, elipsoidal and other similarly shaped particles that do not have sharp edges or points would be considered to be substantially spherical in shape.

The following examples are set forth as representative of the present invention. These examples are not to be construed as limiting the scope of the invention as these and other equivalent embodiments will be apparent in view of the present disclosure, figures, tables, comparative examples and data and accompanying claims.

EXAMPLE 1

Preparation of Styrene/Butylacrylate/Acrylic Acid Polymeric Microsphere

1. Aggregation of Styrene/Butylacrylate/Acrylic Acid Latex:

Pigment dispersion: 7 grams of dry pigment SUN FAST BLUE™ and 1.46 grams of cationic surfactant SANIZOL B-50™ are dispersed in 200 grams of water at 4,000 rpm using a blender.

A polymeric latex is prepared by the emulsion polymerization of styrene/butylacrylate/acrylic acid (82/18/2 parts) in a nonionic/anionic surfactant solution (3 percent) as follows. 352 grams of styrene, 48 grams of butylacrylate, 8 grams of acrylic acid, and 12 grams of dodecanethiol are mixed with 600 milliliters of deionized water in which 9 grams of sodium dodecyl benzene sulfonate anionic surfactant (NEOGEN R™ which contains 60 percent of active component), 8.6 grams of polyoxyethylene nonyl phenyl ether-nonionic surfactant (ANTAROX 897™—70 percent active component), and 4 grams of ammonium persulfate initiator are dissolved. The emulsion is polymerized at 70° C. for 8 hours. The resulting latex contains 60 percent water and 40 percent solids of primarily polystyrene/polybutyacrylate/polyacrylic acid 82/18/2 resin; the Tg of the latex dry sample is 53.1° C., as measured on DuPont DSC; $M_w$=20,000, and $M_n$=6,000 as determined on Hewlett Packard GPC. The particle size of the latex as measured on Brookhaven BI-90 Particle Nanosizer is 160 nanometers.

2. Preparation of Microsphere Size Particles—11.7 Percent of Solids Comprising the Above Resin Particles (95 Percent) and Pigment Particles (5 Percent) and Sheared)

Preparation of the aggregated particles: 208.5 grams of the above prepared SUN FAST BLUE™ dispersion are added to 300 milliliters of water containing 1.5 grams of cationic surfactant alkylbenzyldimethyl ammonium chloride (SANIZOL B-50™). This dispersion is simultaneously added with 325 grams of the above prepared latex into SD41 continuous stirring device (Janke & Kunkel IKA Labortechnik) containing 300 grams of water. The pigment dispersion and the latex are well mixed by the continuous pumping through the shearing chamber operating at a high speed of 10,000 rpm for 8 minutes. A homogeneous blend is obtained, which is then transferred into a kettle placed in a heating mantle, and equipped with mechanical stirrer and temperature probe. The temperature in the kettle is raised from room temperature to 45° C. where the aggregation is performed for 2 hours, while stirring at 400 rpm. Aggregates with a particle size (average volume diameter) of 4.7 and GSD of 1.20 (as measured on the Coulter Counter) are obtained.

Coalescence of aggregated particles: after the above aggregation, 55 milliliters of 20 percent anionic surfactant (NEOGEN R™) are added and the stirring speed is reduced from 400 rpm to 150 rpm. The temperature in the kettle is raised from 45° C. to 85° C. at 1° C./minute. Aggregates of latex and pigment particles are coalesced at 85° C. for 4 hours. After 30 minutes of heating at 85° C., a microsphere particle size of 4.7 microns average volume diameter, and a GSD of 1.20 is obtained as measured on the Coulter Counter. After 4 hours of heating, microsphere particles of 4.6 microns (average volume diameter throughout) with a 1.21 GSD are obtained, indicating that both the particle size and GSD are retained during the coalescence step.

The resulting polymeric microspheres are comprised of poly(styrene-co-butylacrylate-co-acrylic acid), 95 percent, and cyan pigment, 5 percent by weight of particles. The polymeric microspheres are then washed by filtration using hot water (50° C.) and dried on a freeze dryer. The yield of dry polymeric microspheres is 95 percent.

EXAMPLE 2

Preparation of Magnetic Styrene/Butylacrylate/Acrylic Acid Polymeric Microsphere The procedures of Example 1 are repeated, except that the cyan-colored pigment dispersion is replaced by a dispersion of MAPICO BLACK™ to give a magnetic material. The polymer latex is formed as in Example 1, and is mixed with 15 percent by weight of the magnetic material dispersion. The microsphere size particles are prepared and coalesced as described above.

The resulting magnetic polymeric microspheres are comprised of poly(styrene-co-butylacrylate-co-acrylic acid), 85 percent, and MAPICO BLACK™, 15 percent by weight of particles. The polymeric microspheres are then washed by filtration using hot water (50° C.) and dried on a freeze dryer.

EXAMPLE 3

Preparation of Polyester Polymeric Microsphere

1. Preparation of Aspartic Acid Containing Polyester-amine Resin:

A sodiosulfonated random polyester-amine resin containing pendant amine groups and comprised of, on a mole percent basis, approximately 0.415 mole of terephthalate, 0.05 mole of aspartic acid, 0.35 mole of sodium sulfoisophthalate, 0.375 mole of 1,2-propanediol, 0.025 mole of diethylene glycol, and 0.100 mole of dipropylene glycol is prepared as follows.

In a one liter Parr reactor equipped with a bottom drain valve, a double turbine agitator, and a distillation receiver containing a cold water condenser are charged 368.6 grams of dimethylterephthalate, 52 grams of sodium dimethylsulfoisophthalate, 13.31 grams of aspartic acid, 285.4 grams of 1,2-propanediol, 285.4 grams of dipropylene glycol, 26.025 grams of diethylene glycol (1 mole excess of glycols), and 0.8 gram of butyltin hydroxide oxide as the catalyst. The reactor is heated to 165° C. with stirring for 3 hours whereby 115 grams of distillate are collected in the distillation receiver, and which distillate is comprised of about 98 percent by volume of methanol and 2 percent by volume of 1,2-propanediol as measured with the ABBE refractometer available from American Optical Corporation. The mixture is then heated to 190° C. over a one hour period, after which the pressure is slowly reduced from atmospheric pressure to about 260 Torr over a one hour period, and then reduced to 5 Torr over a 2 hour period with the collection of approximately 122 grams of distillate in the distillation receiver, and which distillate is comprised of approximately 97 percent by volume of 1,2-propanediol and 3 percent by volume of methanol as measured by the above ABBE device. The polymer resulting is discharged through the bottom drain valve of the reactor onto a container cooled with dry ice to yield 460 grams of a 3.5 mole percent amine containing sulfonat polyester resin, copoly(1,2-propylene-ethyleneoxy-ethylene-terephthalate)-copoly(copoly(1,2-propylene-ethyleneoxyethylene-sodio-5-sulfoisophthalate-copoly(copoly(1,2-propylene-ethyleneoxyethylene-aspart ate). The sulfonated-amine containing polyester resin glass transition temperature is measured to be 54.1° C. (onset) utilizing the 910 Differential Scanning Calorimeter available from E.I. DuPont operating at a heating rate of 10° C. per minute. The softening point of the resin is measured to be 150.8° C. The number average molecular weight is measured to be 3,500 grams per mole, and the weight average molecular weight is measured to be 5,660 grams per mole using tetrahydrofuran as the solvent. All molecular weights are determined utilizing a Waters 510 HPLC pump, equipped with an autosampler, with samples of about 5 to about 10 grams being passed through 4 styragel HR1 columns calibrated using polystyrene standards and detection using HR 410 Waters DI detector.

2. Preparation of Microsphere Size Particles:

Polymeric microspheres are prepared from and Containing 96 percent by weight of the sulfonated polyester amine, and 4 percent by weight of cyan 15:3 pigment, as follows.

To a 3 liter reaction vessel equipped with a mechanical stirrer is added the sulfonated polyester amine resin (250 grams), into water (2 liters) at 80° C. to yield an emulsion with particles therein, and wherein the particle diameter size is 70 nanometers. The resulting emulsion is cooled down to about 50° C. to about 60° C., and 23 grams of FLEXIVERSE CYAN 15:3 pigment dispersion, available from Sun Chemical, and comprised of 45 percent by weight of the cyan pigment in water, such that the total amount of pigment in the polymeric microspheres is 4 percent by weight, is then added. The resulting mixture is then heated to 56° C., and to this is added 500 milliliters of a 5 percent zinc acetate aqueous solution at a rate of about 1 milliliter per minute. The toner particle size of the mixture is then monitored until it reaches a size (volume average diameter) throughout of 6 microns, after which the reaction mixture is quenched with 500 milliliters of cold water (about 2° C.). The contents of the above reaction vessel are filtered through a 25 micron screen, and the toner product is filtered, redispersed in 2 liters of water for one hour, refiltered a second time, reslurried in 2 liters of water again, refiltered a third time and freeze dried to yield about 205 grams of polymeric microspheres with a particle size of 6 microns and GSD of 1.18 as measured by the Coulter Counter.

EXAMPLE 4

Preparation of Magnetic Polyester Polymeric Microsphere

The procedures of Example 3 are repeated, except that the cyan-colored pigment dispersion is replaced by a dispersion of MAPICO BLACK™ to give a magnetic material. The polymer latex is formed as in Example 3, and is mixed with 15 percent by weight of the magnetic material dispersion. The microsphere size particles are prepared and coalesced as described above.

The resulting magnetic polymeric microspheres are comprised of aspartic acid containing polyester-amine resin, 85 percent, and MAPICO BLACK™, 15 percent by weight of particles. The polymeric microspheres are then washed by filtration using hot water (50° C.) and dried on a freeze dryer.

EXAMPLE 5

Preparation of Radio-labeled Polymeric Microspheres

Polymeric microspheres are prepared as in Examples 1-4, except that a small amount of a combination of yttrium-89 and phosphorus-31, which upon irradiation for a short period of time with an intense thermal neutron flux generated by a nuclear fission reactor, generates yttrium-90 and phosphorus-32, is added to the respective pigment or magnetite dispersions.

The resultant polymeric microspheres include the radioactive precursor components in an amount to be suitable for radio-labeling purposes. The polymeric microspheres exhibit the same particle size and particle size distribution as described above for Examples 1-4.

EXAMPLE 6

Preparation of Antigen-labeled Polymeric Microsphere

Polymeric microspheres are prepared using the processes of Examples 1-4. Following formation of the polymeric microspheres, the microspheres are processed to adsorb an antigen, namely an influenza protein, to the surface of the microspheres.

The antigen attaches well to the microsphere and provides a product suitable for administration to a patient.

The invention claimed is:

1. A method of forming polymeric microspheres for biomedical applications, comprising:
   forming polymeric microspheres by an emulsion/aggregation process from a precursor monomer species; and
   attaching a biomedical functional material selected from the group consisting of a radioactive material, radioactive precursor material, a bioactive agent, and a ligand to said polymeric microspheres,
   wherein said polymeric microspheres have an average particle diameter of from about 1 to about 15 microns with a narrow particle geometric size distribution of less than about 1.25, and
   wherein said emulsion/aggregation process comprises forming a polymeric resin from said precursor monomer species and aggregating and coalescing said polymeric resin into polymeric microspheres.

2. The method of claim 1, wherein said biomedical functional material is a ligand.

3. The method of claim 2, wherein said ligand is a pharmacologically active compound selected from the group consisting of peptides, enzymes, analytes, antigens, and antibodies.

4. The method of claim 2, wherein said ligand is an antigen selected from the group consisting of protein, peptide, polysaccharide, glycoprotein, glycolipid, nucleic acid, and mixtures thereof.

5. The method of claim 1, wherein said biomedical functional material is a radioactive material or a radioactive precursor material.

6. The method of claim 5, wherein said biomedical functional material is selected from the group consisting of yttrium-89, yttrium-90, phosphorus-31, and phosphorus-32.

7. The method of claim 1, wherein said biomedical functional material is a bioactive agent.

8. The method of claim 7, wherein said bioactive agent is a medicament.

9. The method of claim 7, wherein said bioactive agent is selected from the group consisting of antibiotics, antimicrobials, antiseptics, bacteriocins, bacteriostats, disinfectants, steroids, anesthetics, fungicides, anti-inflammatory agents, antibacterial agents, antiviral agents, antitumor agents, growth promoters, and mixtures thereof.

10. The method of claim 1, wherein the biomedical functional material is attached to said polymeric microspheres by at least one of covalent bonding, complexation, physical adsorption and physical absorption.

11. The method of claim 1, wherein the polymeric microspheres are formed from said precursor monomer species and one or more additives.

12. The method of claim 11, wherein the one or more additives are selected from the group consisting of colorants, fluorescent materials, magnetic materials, superparamagnetic materials, and bioactive agents.

13. The method of claim 12, wherein the one or more additives comprises a colorant.

14. The method of claim 12, wherein the one or more additives comprises a magnetic material.

15. The method of claim 14, wherein the magnetic material is a magnetite.

16. The method of claim 12, wherein the one or more additives comprises a superparamagnetic material.

17. The method of claim 12, wherein the one or more additives comprises a bioactive agent.

18. The method of claim 17, wherein the bioactive agent is encapsulated in said polymeric microsphere.

19. The method of claim 1, further comprising surface treating said polymeric microspheres subsequent to said forming step but prior to said treating step, to alter a chemical property of a surface of said polymeric microspheres.

20. The method of claim 19, wherein said chemical property is selected from the group consisting of hydrophobicity, hydrophilicity, surface charge, and presence of functional groups.

21. The method of claim 1, wherein the polymeric microspheres are biocompatible.

22. The method of claim 1, wherein the polymeric microspheres are biodegradable.

23. The method of claim 1, wherein the polymeric microspheres are non-biodegradable.

24. The method of claim 1, wherein said emulsion/aggregation process comprises:
   forming a polymeric resin from said precursor monomer species;
   aggregating said polymeric resin into polymeric particles;
   coalescing said polymeric particles into polymeric microspheres; and
   optionally isolating said polymeric microspheres.

25. The method of claim 1, wherein said emulsion/aggregation process comprises:
   forming a polymeric resin from said precursor monomer species;
   forming an emulsion comprising said polymeric resin;
   coalescing said polymeric resin into polymeric microspheres; and
   optionally isolating said polymeric microspheres.

26. The method of claim 1, wherein said emulsion/aggregation process comprises:
   providing a polyester resin formed from said monomeric species;
   dispersing said polyester resin in an aqueous media optionally comprising a surfactant, to provide a suspension of suspended particles of said polyester resin;
   homogenizing said suspension;
   aggregating and coalescing said homogenized suspension by adding a cationic metal salt and optional additives, and heating the aggregates, to form polymeric microspheres; and
   optionally isolating said polymeric microspheres.

27. The method of claim 26, wherein said hearing is conducted at or near a glass transition temperature of the polyester resin.

28. The method of claim 1, wherein a polymer formed from said precursor monomer species is a functionalized polymer.

* * * * *